US008802179B2

(12) United States Patent
Miller

(10) Patent No.: US 8,802,179 B2
(45) Date of Patent: Aug. 12, 2014

(54) NON-DIGESTIBLE SUGAR-COATED PRODUCTS AND PROCESS

(76) Inventor: Guy W. Miller, Princeton, MN (US)

(*) Notice: Subject to any disclaimer, the term of this patent is extended or adjusted under 35 U.S.C. 154(b) by 0 days.

(21) Appl. No.: 13/090,077

(22) Filed: Apr. 19, 2011

(65) Prior Publication Data
US 2011/0206800 A1  Aug. 25, 2011

Related U.S. Application Data

(63) Continuation of application No. 12/362,858, filed on Jan. 30, 2009, now abandoned, which is a continuation of application No. 10/686,129, filed on Oct. 14, 2003, now abandoned, which is a continuation of application No. PCT/US02/12323, filed on Apr. 17, 2002.

(60) Provisional application No. 60/284,389, filed on Apr. 17, 2001.

(51) Int. Cl.
A23L 1/302 (2006.01)
A23L 1/304 (2006.01)
A23G 3/00 (2006.01)
A61K 9/36 (2006.01)
A61K 9/50 (2006.01)
A61K 47/26 (2006.01)
A61K 31/70 (2006.01)
A61K 9/28 (2006.01)
A61K 9/48 (2006.01)

(52) U.S. Cl.
CPC ............. A61K 9/286 (2013.01); A61K 9/5036 (2013.01); A61K 9/4891 (2013.01)
USPC ............ 426/648; 426/658; 426/103; 426/72; 426/442; 424/493; 424/442; 514/777; 514/23

(58) Field of Classification Search
None
See application file for complete search history.

(56) References Cited

U.S. PATENT DOCUMENTS

| 4,681,771 | A  | 7/1987  | Adachi et al.      |
| 4,927,811 | A  | 5/1990  | Quarles            |
| 5,032,579 | A  | 7/1991  | Speights et al.    |
| 5,219,842 | A  | 6/1993  | Okada et al.       |
| 5,576,020 | A  | 11/1996 | Iritani et al.     |
| 5,688,777 | A  | 11/1997 | Garleb et al.      |
| 5,776,524 | A  | 7/1998  | Reinhart           |
| 5,827,526 | A  | 10/1998 | Dohnalek et al.    |
| 5,866,619 | A  | 2/1999  | Sintov et al.      |
| 6,194,379 | B1 | 2/2001  | McEwen et al.      |
| 6,200,605 | B1 | 3/2001  | Day                |
| 6,203,797 | B1 | 3/2001  | Perry              |
| 6,221,350 | B1 | 4/2001  | Brown et al.       |
| 6,368,629 | B1 | 4/2002  | Watanabe et al.    |
| 6,436,453 | B1 | 8/2002  | van Lengerich et al.|
| 6,451,344 | B1 | 9/2002  | Sotoyama et al.    |
| 6,468,568 | B1 | 10/2002 | Leusner et al.     |
| 6,475,540 | B1 | 11/2002 | Howling et al.     |
| 6,750,331 | B1 | 6/2004  | Takaichi et al.    |

FOREIGN PATENT DOCUMENTS

| JP | 03-076561  | 4/1991 |
| JP | 2001048808 | 2/2001 |

OTHER PUBLICATIONS

Bezkarovainy, "Probiotics: Determinants of Survival and Growth in the Gut," Am. J. Clin. Nutr., 2001, p. 399S-405S, vol. 73 (suppl.).
Bouhnik et al., "Short-Chain Fructo-Oligosaccharide Administration Dose-Dependingly Increases Fecal Bifidobacteria in Healthy Humans," Journal of Nutrition, 1999, p. 113-116, vol. 129.
Campbell et al., "Selected Indigestible Oligosaccharides Affect Large Bowel Mass, Cecal and Fecal Short-Chain Fatty Acids, pH and Microflora in Rats," J. Nutr., 1997, p. 130-136, vol. 127.
Cummings et al., "Prebiotic Digestion and Fermentation," Am. J. Clin. Nutr., 2001, p. 415S-420S, vol. 73 (suppl.).
Djouzi et al., "Copared Effects of Three Oligosaccharides on Metabolism of Intestinal Microflora in Rats Inoculated with a Human Fecal Flora," British Journal of Nutrition, 1997, p. 313-324, vol. 78.
Ellegard et al., "Inulin and Oligofructose do not Influence the Absorption of Cholesterol, or the Excretion of Cholesterol, Ca, Mg, Zn, Fe, or Bile Acids but Increases Energy Excretion in Ileostomy Subjects," European Journal of Clinical Nutrition, 1997, p. 105, vol. 51.
Gibson et al., "Dietary Modulation of the Human Colonic Microbiota: Introducing the Concept of Prebiotics," Journal of Nutrition, 1995, p. 1401-1412, vol. 125.
Hussein et al., "Selected Fructooligosaccharide Composition of Pet-Food Ingredients," J. Nutr., 1998, p. 2803S-2805S, vol. 128.
Jenkins et al., "Inulin, Oligofructose and Intestinal Function," Journal of Nutrition, 1999, p. 1431S-1433S, vol. 129.
Kaufhold et al., "Fruco-Oligosaccharide Supplementation: Effects on Metabolic, Endocrine and Hematological Traits in Veal Calves," Journal of Veterinary Medicine, 2000, p. 17-29, vol. 47, No. 1.
Kleessen et al., "Effects of Inulin and Lactose on Fecal Microflora, Microbial Activity, and Bowel Habit in Elderly Constipated Persons," Am J of Clin Nutr, 1997, p. 1397-1402, vol. 65.
Loo et al., "Functional Food Properties of Non-Digestible Oligosaccharides: A Consensus Report from the ENDO Project (DGXII AIRII-CT94-1095)," British Journal of Nutrition, 1999, p. 121-132, vol. 81.
Molis et al., "Digestion, Excretion, and Energy Value of Fructooligosaccharides in Healthy Humans," Am J of Clin Nutr, 1996, p. 324-328, vol. 64.
Mul, "Application of Oligosaccharides in Animal Feeds," Proceedings: International Symposium on Non Digestible Oligosaccharides: Health Food for the Colon?, 1997, Wagneningen, Netherlands.

(Continued)

Primary Examiner — Savitha Rao
Assistant Examiner — Gregg Polansky
(74) Attorney, Agent, or Firm — Sunstein Kann Murphy & Timbers LLP

(57) ABSTRACT

A method and composition are provided for coating a component to achieve colon-targeted delivery. A component is coated with a fructose-based non-digestible carbohydrate such as a inulin, fructo-oligosaccharide or neosugar. The coated component is orally administered to a monogastric animal. The non-digestible coating causes the composition to pass through the stomach and small intestine without being degraded, and delivers the component to the colon where the coating is digested by microbial fermentation and the component is released.

20 Claims, 3 Drawing Sheets

(56) References Cited

OTHER PUBLICATIONS

Nilsson et al., "Availability of Cereal Fructans and Inulin in the Rat Intestinal Tract," Journal of Nutrition, 1986, p. 1482-1486, vol. 86.

Oku et al., "Digestion, Absorption, Fermentation and Metabolism of Functional Sugar Substitutes and Their Available Energy," Pure and Applied Chemistry, 2002, p. 1253-1261, vol. 74, No. 7.

Roberfroid et al., "The Bifidogenic Nature of Chicory Inulin and its Hydrolysis Products," Journal of Nutrition, 1989, p. 11-19, vol. 128.

Simon et al., "Intestinal Floral in Health and Disease," Gastroenterology, 1984, p. 174-193, vol. 86.

Wang et al, "Effects of the in vitro Fermentation of Oligofructose and Inulin by Bacteria Growing in the Human Large Intestine," Journal of Applied Bacteriology, 1993, p. 373-380, vol. 75.

NON-DIGESTIBLE SUGAR-COATED PRODUCTS AND PROCESS

CROSS REFERENCE TO RELATED APPLICATION

This application is a continuation of U.S. application Ser. No. 12/362,858, filed Jan. 30, 2009, which is a continuation of U.S. application Ser. No. 10/686,129, filed Oct. 14, 2003, which is a continuation of PCT/US02/12323 filed Apr. 17, 2002, which claims the benefit of U.S. Provisional Application Ser. No. 60/284,389, filed Apr. 17, 2001, all of which are incorporated herein by reference in their entirety.

BACKGROUND

1. Field of the Invention

This invention is directed to methods and compositions for colon-targeted delivery of components.

2. Description of the Prior Art

Fructan is a non-structural carbohydrate and is a polymer of fructose. Fructans have a general structure of a glucose linked to multiple fructose units. There are several types of fructans present in nature, and they can broadly be divided into 3 groups: inulins, fructo-oligosaccharides (FOS), and neosugars.

Inulin is a polydisperse fructan extracted from plants, including chicory root, asparagus shoot, banana, dandelion, garlic, globe artichoke, Jerusalem artichoke, leek, onion, rye, salsify, and wheat, that has not been digested enzymatically by inulinase. The chemical structure of inulin is shown in FIG. 1. $GF_n$ is a glucose ending fructan chain, and n represents chain length. Inulin has a degree of polymerization (DP) in the approximate range of 2 to 60 units of β (2-1) fructose with a glucosyl terminus. The average DP is greater than 10 units.

Fructo-oligosaccharide (FOS) is partially hydrolyzed inulin with a DP in the approximate range of 2 to 20 units of β (2-1) fructose with either a glucosyl or a fructosyl terminus. The average DP is less than 10 units. Chemical structures of glucose ending fructan chains ($GF_n$) and fructose ending chains ($F_n$) are shown in FIGS. 2A and 2B. Inulin is hydrolyzed with inulinase, for example, to produce fructo-oligosaccharides.

Neosugars are fructo-oligosaccharides that can be prepared, for example, by an enzymatic reaction using sucrose and the enzyme fructosyltransferase from an organism such as *Aspergillus niger*. The chemical structure of neosugar is shown in FIG. 3.

Neosugars have DP in the approximate range of 2 to 4 units of β (2-1) fructose with a glucosyl terminus. The average DP is about 2 to 3 units. Collectively, inulin, FOS, and neosguars are referred to herein as fructans.

Fructans are currently used as an animal feed supplement, mixed with the animal feed. Fructans are found in the feed of monogastric animals, including poultry, turkey, swine, dog, cat, horse, and bovine calf diets. (Bovine calves begin their development as monogastric mammals). Fructans are also added to food and drink for human consumption. As an oral supplement, fructans have been shown to improve weight gain, reduce fecal odor, reduce colon cancer, lower blood triglycerides, increase mineral uptake, and promote a healthy gastrointestinal system.

Fructans are essentially "non-digestible" by monogastrics; they are not digested in the stomach or small intestines. Consequently, the fructan-coated components of the instant invention are not digested in the stomach of monogastric mammals and pass directly to the colon where the fructan is fermented by organisms residing in the colon. As fructan-fermenting bacteria grow, there is a concomitant decrease in the concentrations of putrefactive bacteria such as *Escherichia coli*, *Clostridium perfringens* and *Salmonella*, which are widely known to produce malodorous aromatic metabolites. Bacteria that utilize fructans as a source of energy include beneficial bacteria in the genus of *Bifidobacterium* and *Lactobacillus*. Non-digestible ingredients, such as fructans, that beneficially affect the host by selectively stimulating the growth and/or activity of bacteria in the colon that can improve host health and known as "prebiotics".

Wang et al. (Journal of Applied Bacteriology, 75:373-380, 1993) looked at mixed populations of colonic bacteria in a batch culture grown on inulin, fructo-oligosaccharide, polydextrose and starch. The type of carbohydrate used in each batch culture had no effect on total aerobic, anaerobic or *Bacteriodes* counts. *Bifidobacteria* counts were 5 to 13 times higher with batch cultures grown on fructo-oligosaccharide and inulin then polydextrose and starch. The coliform counts were 8 to 630 times lower with batch cultures grown on inulin and fructo-oligosaccharide than polydextrose and starch. *Lactobacillus* counts were 316-1,000 times lower in batch cultures when inulin was used as a substrate than fructo-oligosaccharide, starch and polydextrose.

In order for inulin and fructo-oligosaccharides to affect the microbial population in the colon, they must first pass through the stomach and small intestine. Samples taken from the ileum of humans receiving diets containing inulin or fructo-oligosaccharides have been shown to exhibit an 89% and 88% recovery respectfully (Ellegård et al., European Journal of Clinical Nutrition, 51:1-5, 1997). Similarly, humans receiving Neosugar in their diet have been shown to exhibit an 89% recovery in ileal samples taken (Molis et al., American Journal of Clinical Nutrition, 64:324-328, 1996). The fraction of fructan that is not recovered is digested in the gastrointestinal tract and then absorbed as glucose or fructose. The digestion may have occurred in the ileum via bacterial fermentation or by acid digestion in the stomach (Simon et al., Gastroenterology, 86:174-193, 1984). In vitro studies have shown that fructans and inulin are hydrolyzed at a low rate and a very low pH (Nilsson et al., Journal of Nutrition, 86:1482-1486, 1988).

Once the fructans reach the colon, they are fermented completely by the microbial flora. (Jenkins et al., Journal of Nutrition, 129:1431S-1433S, 1999). With fermentation of the fructans in the colon, changes occur to the microbial flora. Most notably, the *Bifidobacteria* sp., has been shown to increase 5 to 63 fold (Djouzi et al., British Journal of Nutrition, 78:313-324, 1997). A review by Loo et al. (British Journal of Nutrition, 81:121-132, 1999) of ten trials studying the increase in *Bifidobacteria* sp. in the colon of humans receiving inulin or fructo-oligosaccharide in their diets showed a statistically significant increase in *Bifidobacteria* sp. The average for the nine trials was an 11.8-fold increase in *Bifidobacteria* sp. with a high of a 22-fold increase. Other changes that were observed in colonic populations of humans receiving inulin and fructo-oligosaccharide include the significant decrease in *Bacteriodes* sp. and/or *Clostridia* sp. (Gibson et al., Journal of Nutrition, 125:1401-1412, 1995; Kleessen et al., American Journal of Clinical Nutrition, 65:1397-1402, 1997).

The increase of *Bifidobacteria* has been shown to be correlated to a dose response to fructan addition to the diet. Studies have shown that humans subjects exhibit no increase in *Bifidobacteria* sp. until their diet contains 10 grams of Neosugar per day (Bouhnik et al., Journal of Nutrition, 129:113-116, 1999). A review by Roberfroid et al. (Journal of Nutrition, 128:11-19, 1998) combined data for inulin, fructooligosaccharide and Neosugar and concluded that log increases in counts do not correlate to daily doses administered. One variable considered to correlate with increases was the initial number of *Bifidobacteria* in the feces. It appeared that the lower the initial number, the greater the increase whatever the dose, within the range of 4 to 20 or more grams per day. Consuming a few grams of any of these fructans daily could be sufficient to cause a significant increase in colonic *Bifidobacteria*.

SUMMARY OF THE INVENTION

According to one embodiment of the present invention, a method and composition are disclosed for coating a component to achieve colon-directed delivery. The invention includes coating a component with a non-digestible composition, such as a fructan, to produce a feed supplement. The coated component, a non-digestible coated composition, is administered to a monogastric animal, where the non-digestible coated composition passes through the stomach and small intestine without being degraded, and is delivered to the colon where the coating is digested and the component is released.

According to a preferred embodiment of the present invention, the indigestible coating is fructan.

DETAILED DESCRIPTION OF THE INVENTION

Figure 1:
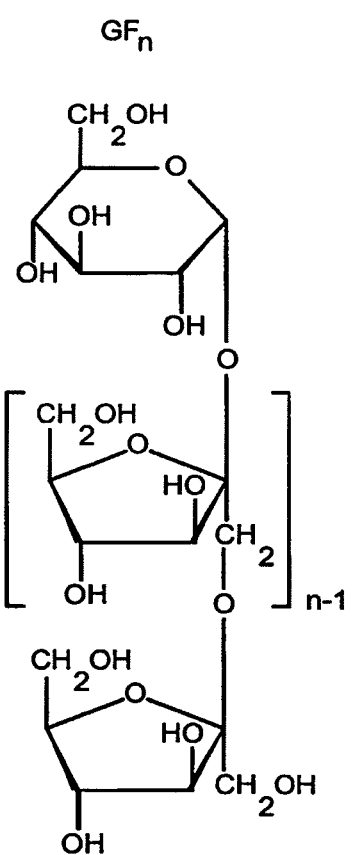
FIG. 1 shows the chemical structure of inulin.
Figure 2A:
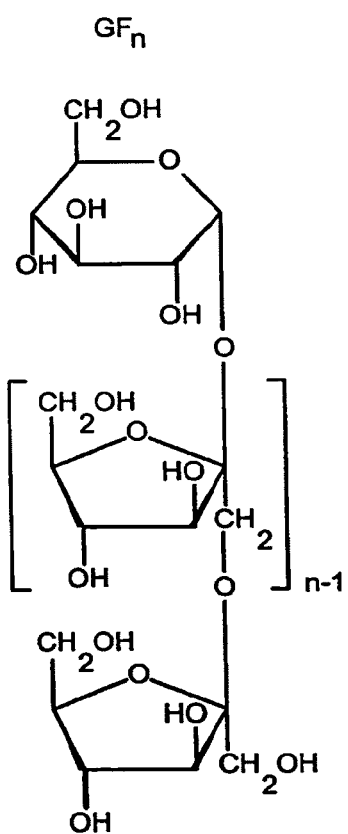
FIGS. 2A and 2B show chemical structures of fructo-oligosaccharides.
Figure 2B:
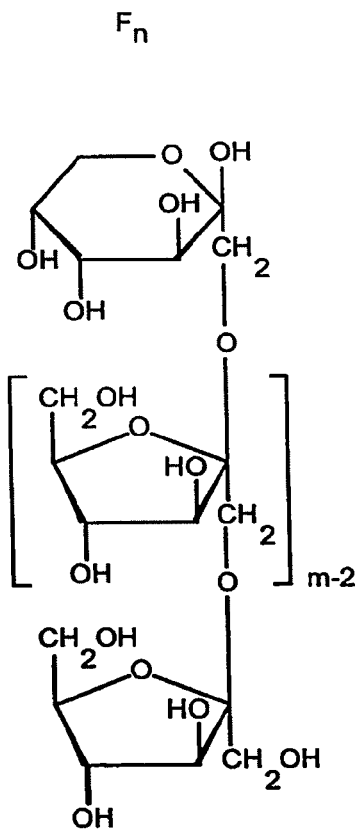
Figure 3:
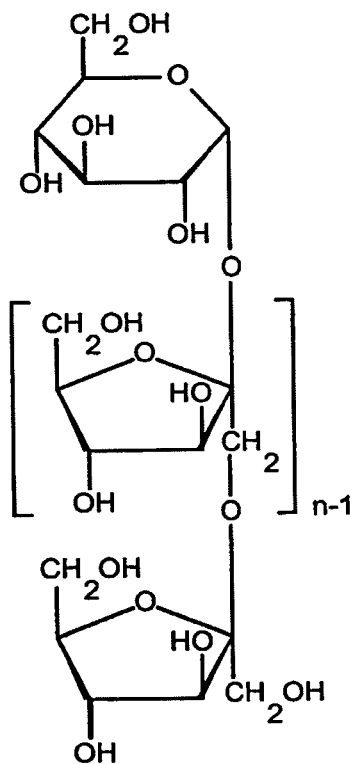
FIG. 3 shows the chemical structure of neosugar.

The present invention is directed to a method and composition for coating a component for delivery targeted to the colon of an animal. It is often desirable to deliver components, such as drugs, vitamins, minerals, metabolites, beneficial bacteria, and other molecules, to the colon of an animal without subjecting the component to the acids and digestive enzymes of the stomach and small intestine.

Administration by conventional means, including oral, intravenous, percutaneous, or other known delivery methods, generally results in reduced bioavailability of the component. Degradation or alteration of the component by digestive enzymes and/or low pH may occur in the stomach and small intestine when conventional oral preparations are used, reducing or inactivating the therapeutic activity of the component.

Intravenous and percutaneous administration generally requires a large dosage, sufficient to ensure that the desired level of the component reaches the colon. Such routes of administration are generally not suitable for components such as beneficial bacteria and many vitamins, minerals and metabolites.

Drugs can be targeted to the colon by coating the drug formulations with polymeric coatings, such as acrylic acid derivatives or cellulose derivatives, that can withstand both low and slightly basic pH values for several hours. A disadvantage of this targeting method is the uncertainty of location and environment in which the polymeric coating will be degraded. The delay in coating degradation is based on the amount of time spent in a particular pH environment. If the coated drug is delayed in the upper gastrointestinal tract, such as for mechanical reasons, the drug may be released in a non-target location, such as the small intestine.

The present invention provides a safe and effective method and composition for targeting components specifically to the colon based on the presence or absence of bacteria that degrade a prebiotic, such as fructan. The components to be administered are coated with a prebiotic that is not digested in the stomach or small intestine, but that is degraded by bacteria present in the colon, especially of monogastric animals.

As used herein, "prebiotic" is intended to mean a non-digestible food ingredient that beneficially affects the host by selectively stimulating the growth and/or activity of one or a limited number of bacteria in the colon, that can improve host health. Oligosaccharides such as inulin, fructo-oligosaccharide and neosugar, which cannot be digested except through bacterial activity, are considered prebiotics. Many other carbohydrates can be considered prebiotics, for example, those listed in Table 1. Other ingredients that reach the colon undigested and can be considered prebiotics include peptides, proteins, and lipids. Criteria for classifying a substance as a prebiotic may include:

1. Not hydrolyzed or absorbed in the upper part of the gastro-intestinal tract.
2. Selectively fermented by potentially beneficial bacteria in the colon.
3. Alters the composition of the colonic microbial flora towards a healthier composition.
4. Preferably, induces effects that are beneficial to the host health.

TABLE 1

Candidate Prebiotic Carbohydrates

| Oligosaccharide | Chemical Composition |
| --- | --- |
| Fructo-oligosaccharide | β(2-1) fructan with degrees of polymerization ranging from 2-20 units and has an average degrees of polymerization of 2 to 10 |
| Inulin | β(2-1) fructan with degrees of polymerization ranging from 2-60 units and has an average degrees of polymerization greater than 10 |
| Neosugar | β(2-1) fructan with degrees of polymerization ranging from 2-4 units and has an average degrees of polymerization from about 2 to about 3 |
| Polydextrins | Complex mixture of glucose-containing Oligosaccharide |
| Transgalactosylated oligosaccharides | Mainly 6' galactosyllactose, DP of oligosaccharide fraction 2-5 (primarily DP 3); 55% pure |
| Galacto-oligosaccharides | Oligogalactose (85%), small amounts of glucose, galactose, and lactose |
| Soya oligosaccharides | Stachyose (fructose, galactose, galactose, glucose) and raffinose (fructose, galactose, glucose), DP 3-4 |
| Xylo-oligosaccharides | B(1-4) linked xylose; 70% pure, DP of oligosaccharide fraction is 2-4 |
| Isomalto-oligosaccharides | Mixture of α(1-6) linked glucose oligomers (isomaltose, panose, isomaltotriose) |
| Lactulose | Galactose and fructose-containing disaccharide |

DP = Degrees of polymerization

Many bacteria can utilize fructans for growth. These include lactic acid bacteria, such as *Lactobacillus* sp. and *Bifidobacterium* sp., which are considered probiotics. Many bacteria, such as, *Escherichia coli* and *Salmonella* sp. cannot utilize fructans for growth.

As used herein, "non-digestible" is intended to mean that a substance taken orally is substantially resistant to chemical and enzymatic degradation in the stomach and small intestine, but is susceptible to degradation in the colon.

As used herein, "monogastric" is intended to encompass any animal having one stomach. Examples of monogastric animals include, but are not limited to, horses, emu, ostrich, dog, cat, swine, bear, turkey, chickens, ducks, quail, pheasants, reptiles, and humans. Pre-ruminant animals such as young cattle, buffalo, bison, and elk are also encompassed by the term monogastric as these animals are born monogastric and then develop into true ruminants as adults.

Additionally, the compositions and methods of the present invention are suitable for any animal that breaks down fructose-based oligosaccharide selectively in a specific part of the gastrointestinal tract. Breakdown of a fructose-based oligosaccharide generally requires the presence of bacteria capable of fermenting the oligosaccharides, such as those from the genus *Bifidobacterium* and *Lactobacillus*. The compositions of the invention can be selectively delivered to the colon by administration of the coated composition to any animal having fructan-fermenting bacteria present in at least part of their digestive tract. For those animals having insufficient Fructan-fermenting bacteria in their digestive tract, Fructan digesting bacteria can be optionally added along with the diet.

As used herein, "component" is intended to encompass any compound, molecule composition, or organism that is to be coated and delivered to the colon in the method of the invention. Examples include, but are not limited to, minerals, vitamins, drugs, bacteria, yeast, immune stimulators, nutrients, nutraceuticals, electrolytes, chelated minerals, molds, enzymes, energy-providing compounds, antibodies, and acids.

Minerals for colon-targeted delivery include, but are not limited to, calcium, chromium, cobalt, copper, iodine, iron, magnesium, manganese, organic trace minerals, phosphorus, potassium, selenium, sodium, sulfur, zinc, and the like. Vitamins include, but are not limited to, vitamins A, B12, C, D, E, K, betaine, biotin, choline, folic acid, inositol, niacin, pantothenic acid, pyridoxine, riboflavin, thiamine, etc. Drugs include, but are not limited to, antibiotics, anti-viral agents, anti-mold agents, bloat preventatives, coccidiostats, growth enhancers, vaccines, wormers, chemotherapy agents, anti-tumor agents, insulin, etc. Examples of suitable drugs include Aureomycin® 90, Aureomix® 500, BMD® 60, Chlor-Max™-SP 500, Denagard® 10, Lincomix® 50, Mecadox® 10, Neo-Terramycin® 50/50, Pulmotil® 90, Tylan® 100, and 3-Nitro® 20.

Bacteria to be introduced into the colon include any beneficial bacteria, including, but not limited to, *Bacillus coagulans, Bacillus lentus, Bacillus licheniformis, Bacillus pumilus, Bacillus subtilis, Bacteroides amylophilus, Bacteroides capillosus, Bacteroides ruminocola, Bacteroides suis, Bifidobacterium adolescentis, Bifidobacterium animalis, Bifidobacterium bifidum, Bifidobacterium infantis, Bifidobacterium longum, Bifidobacterium thermophilum, Entercoccus cremoris, Entercoccus diacetilactis, Entercoccus faecium, Entercoccus intermedius, Entercoccus lactis, Entercoccus thermophilus, Lactobacillus acidophilus, Lactobacillus brevis, Lactobacillus bulgaricus, Lactobacillus casei, Lactobacillus cellobiosus, Lactobacillus curvatus, Lactobacillus delbruekii, Lactobacillus fermentum, Lactobacillus helveticus, Lactobacillus lactis, Lactobacillus plantarum, Lactobacillus reuteri, Leuconostoc mesenteroides, Pediococcus acidilactici, Pediococcus cerevisiae, Pediococcus pentosaceus, Pripionibacterium freudenreichii, Propionibacterium sherimanii, Streptococcus cremoris, Streptococcus diacetilactis, Streptococcus faecium, Streptococcus intermedius, Streptococcus lactis, and Streptococcus thermophilus*.

Yeast include, but are not limited to, *Saccharomyces* sp. and *Candida* sp., more specifically *Saccharomyces cerevisiae* and *Candida utilis*. Immune stimulators include, but not limited to, mannose-oligosaccharide and beta-glucan. Nutrients include, but are not limited to, amino acids such as arginine, glycine, lysine, methionine, taurine, threonine and tryptophan, peptides such as insulin, proteins, carbohydrates, amino acids, bone meal, grains, egg, fats and oils, feather meal, fish meal, plant and animal byproducts, plasma, poultry byproducts, whey, and the like.

Nutraceuticals include, but are not limited to, spices, essential oils, soy products and natural extractives such as alfalfa, angelica, anise, basil, bay leaf, calendula, camomile, caraway, cardamom, carrot, cayenne pepper, chicory, celery seed, chives, cinnamon, cloves, coriander, cumin, dandelion, dill, fennel, fenugreek, garlic, glycyrrhiza, habanero pepper, horehound, horsemint, horseradish, hyssop, gentian, ginger, ginseng, juniper, kava, lemon balm, lemon grass, licorice, marjoram, melissa, mustard, netmeg, nettle, onion, oregano, parsley, pepper, peppermint, raspberry, rosemary, rue, savory, spearmint, tarragon, thyme, and vanilla.

Nutraceuticals also include, but are not limited to, herbs such as Boneset or Feverwort (*Eupatorium perfoliatum*), Burdock (*Arctium lappa*), Coltsfoot (*Tussilago farfara*), Comfrey (*Symphytum officinale*), Devil's Claw Root (*Harpagophytum procumbens*), Ginkgo (*Ginkgo biloba*), Golden Rod (*Solidago virgaurea*), pot Marigold (*Calencula officinalis*), Meadowsweet (*Filipendula ulmaria*), Monk's Pepper or Chasteberry (*Vitex agnus-castus*), Nettle (*Urtica dioicea*), Red Poppy Seed (*Papaver rhoeas*), Raspberry leaves (*Rubidus idaeus*), Valerian root (*Valeriana officinalis*), Vervain (*Verbena officinalis*), and Yellow Dock (*Rumex crispus*).

Electrolytes include, but are not limited to, potassium, magnesium, and calcium. Chelated minerals include, but are not limited to, copper, zinc, iron, manganese, chromium and magnesium bound to a protein or carbohydrate source. Examples include, but are not limited to Alframin® from RK Marketing Enterprises, Inc. (Waconia, Minn.) and SQM™ from Quali Tech Inc. (Chaska, Minn.). Other companies that produce chelated minerals include Albion Laboratories, Inc. (Clearfield, Utah), Zinpro Corporation (Eden Prairie, Minn.) and Chelated Minerals (Ogden, Utah). Molds include, but are not limited to, *Aspergillus niger* and *Aspergillus oryzae*. Enzymes include, but are not limited to, cellulose, hemicellulase, amylase, phytase, and ligninase. Energy-providing compounds include, but are not limited to, sugars such as glucose, sucrose, fructose, propylene glycol and glucose precursors.

Antibodies include, but are not limited to, those reactive with specific bacteria and viruses and those reactive with broad classes of bacteria and viruses. Acids include, but are not limited to, citric acid, lactic acid, and acetic acid. Additionally, other components, including emulsifiers and surfactants, acidifiers, buffers, dietary fiber, flavoring agents, attractants, flow and anti-caking agents, grit, kelp meal, algae, molasses, pigments, preservatives, antioxidants mold inhibitors, sweeteners, urea, yucca products, and other components, can be coated by the method of the invention for colon-targeted delivery.

In another embodiment of the present invention, the fructan coating is used to mask or cover-up an otherwise unpalatable component. Examples of unpalatable components include, but are not limited to, ammonium chloride, calcium sulphate, magnesium chloride, propylene glycol, drugs, vitamins, and other ingestible compositions. In this instance, the Fructan coating is provided to provide a more organoleptic composition.

In a further embodiment of the present invention, the fructan coating is used to prevent or minimize the release of components that may be disruptive or harmful to the stomach or small intestine. For example, chemotherapy and anti-tumor agents directed to a tumor in the colon may cause undesirable effects if released in the upper gastrointestinal tract.

The coating of the present invention can also be used to improve the flowing characteristics of a component. This is especially beneficial for components that are sticky, powdery, viscous, etc. in their uncoated state.

The coating can be applied by conventional methods, including freeze-drying, spray-coating, mixing, agglomeration, and combining a rapid centrifugal application of liquid and powder to create a thin film polymer coating using a rotary disc type liquid/powder applicator.

In one embodiment, the component to be delivered to the colon is coated with fructan using a rotary driven disc system. The component can be in the form of pellets, tablets, pieces, nuggets, crumbles, and the like, that may be of any size, and may be regular or irregular in shape. The pellets may be, for example, in the approximate size range of 10 microns to 100 microns in diameter. In this system, the pellets are dropped on the disc as it rotates. This rotation carries the pellet out to the chamber wall by centrifugal force. As the pellet is turned by mixing blades mounted on the chamber walls, powdered fructan and liquid or a mixture of the fructan and liquid are introduced into the chamber. Liquid, such as water or a mixture of water and fructan, is atomized by the high-speed disc into ultra-fine particles that are applied to the pellets. The process results in a thin film coating of the carbohydrate on the component pellets.

Probiotic bacteria such as *Lactobacillus* sp. and *Bifidobacteria* sp. are known for their ability to ferment fructans while *Escherichia coli* and *Salmonella* sp. cannot. In the colon, this positive change in the microbial population leads to a healthier intestinal tract which improves immune response, weight gain, feed efficiency, nitrogen retention, mineral absorption and increased short-chain fatty acids production. Other positive benefits include reduced colonization of the intestinal tract by enteric bacteria, reduced diarrhea, reduced stomach upsets, firmer feces and an increased energy source for hyperglycemic animals such as dogs, cats and veal calves.

The chain length of the fructan is fermented differently by different species of probiotic bacteria. The longer DP fructan is fermented half as fast as fructans with shorter DP. A coating composition having a longer chain length such as inulin may be well suited for a positive prebiotic effect throughout the colon. Fructo-oligosaccharide and Neosugar are considered a shorter DP fructans, and may be well suited for quick delivery to the colon. Combinations can produce a variety of degradation effects, as desired.

Pure cultures of different species of *Bifidobacteria* have been shown to have different growth rates when grown on fructo-oligosaccharide. In other studies mixed cultures of *Bifidobacterium infantis, Escherichia coli* and *Clostridium perfringens* grown on fructo-oligosaccharide have shown an inhibitory effect towards *Escherichia coli* and *Clostridium perfringens*.

The favorable effects of soluble fiber for diabetes mellitus may also be favorable for veal calves. Veal calves in late fatting periods often develop hyperglycemia, glucosuria, and insulin resistance with high lactose intakes. Kaufhold et al. (Journal of Veterinary Medicine 47(1):17-29,2000) has reported higher weight gains in veal calves receiving fructo-oligosaccharide. The study also showed calves receiving fructo-oligosaccharide had a lower post-prandially increase in glucose and higher insulin concentrations. They concluded that fructo-oligosaccharide has similar endocrine traits in veal calves as in humans with diabetes mellitus. Mul ("Application of Oligosaccharides in Animal Feeds", in Proceedings: International Symposium on Non Digestible Oligosaccharides: Health Food for the Colon?, Wagneningen, Netherlands, 1997) reported on field trials by Trouw Nutrition from 1990-1992 with veal calves. The majority of the field trials showed improved weight gain (0.8-2.4 kg), improved feed efficiency (3-14%), reduction in diarrhea incidence, and on average firmer feces. In one reported trial, higher weight gains were observed when a probiotic was used in combination with fructo-oligosaccharide.

The amount of the component to be administered will vary depending on the desired effect to be achieved, and depending on the species, age, sex, physical condition, disease state, disease progression, etc., of the subject receiving the component. When the component is a drug, the amount administered will also depend on the drug's efficacy. In general, it would be expected that the dosage of drug required to achieve a particular result, and delivered directly to the colon, will be less than the dosage required for intravenous, conventional oral or other systemic delivery.

Example 1

Coated Polypropylene Glycol in Dairy Cows

In this coating trial, the propylene glycol product (Glycopulp™) was coated with FOS (bioSecure™) as the coating agent. The use of propylene glycol as a glucogenic supplement for dairy cows during the transition phase from the middle of the dry period through the first 21 days is known. However, the addition of propylene glycol to the total mixed ration (TMR) is known to decrease feed intake.

The propylene glycol product (Glycopulp™) was masked with a feed flavor, and coated with FOS as the coating agent. The drying agent was chicory pulp and the flavoring agent was Milk Buds™ F.S.

Glycopulp™ is a blend of chicory pulp (1 mm screen) and feed grade propylene glycol in a ratio of 55:45 (W/W). The Glycopulp™ was supplied by Socode S.C. (Warcoing, Belgium). Chicory pulp (1 mm screen) was used as a drying agent during the coating process. The FOS used as the coating agent was suspended in water prior to coating.

The flavoring agent, Milk Buds™ F.S. (Lot No. 8176) was supplied by QualiTech (Chaska Minn., Product Code 2741). The flavoring agent can be added to feed, for example, at a rate of about 0.25-4 ounces per ton of finished feed. In this trial, a rate of approximately 2 ounces per ton of finished feed was used. The flavoring agent was suspended in water with the FOS prior to coating.

Coating Process

Engineered Technology Systems, Inc. (ETS, Gilroy, Calif.) offers coating equipment to the agricultural seed market sector, manufactured food industries and pharmaceutical industry. The approach to the ETS line of coating systems is the rapid application of liquid and powder materials to create a thin film polymer coating, build-up coating or spherical pellet. The system "coats" products by centrifugal force as the product travels rapidly around the stator (bowl) via the movement of a rotor. The rotor is the bottom end of the equipment that moves the product by centrifugal force. The atomizer sits slightly above the rotor. The atomizer is a small spinning disk through which liquids are pumped via peristaltic pumps at precise rates. When liquids hit the atomizer the liquids are atomized into small particles that are projected onto the materials being moved around the stator. Powders can be injected into the coating equipment at any time during the process to allow a "build-up" process to form around a nucleolus (nucleolus being the product coated). The equipment achieves all of these functions by computerized controls that monitor and provide operator feedback. The entire coating process is a controlled semi-continuous system where a known amount of material is coated at one time. The production rate of each coating run takes only seconds to achieve the desired product.

Trial 1

The proportions of components used for this trial are found in the table below. Three hundred twenty grams of polyethylene glycol (Glycopulp™) was placed into the drum of the ETS R-12 rotary coater. The moving rotor was turned on and it was determined that the sample adequately flowed in the equipment to be coated. Thirty two milliliters of Stock Solution A (FOS and water) was applied to the rotating Glycopulp™. After applying Stock Solution A, 17.5 grams of chicory pulp (1 mm screen size) was applied as a drying agent. Drying can also be achieved by low temperature air.

| Trial One, No Flavor Added | |
|---|---|
| Item | Amount |
| Stock Solution A: | |
| bioSecure ™ FOS | 11 grams |
| Water | 2 liters |
| Glycopulp | 320 grams |
| hicory Pulp | 17.6 grams |

Trial 2

The proportions of components used for this trial are found in the table below. Three hundred twenty grams of Glycopulp™ was placed into the drum of the ETS R-12 rotary coater. The moving rotor was turned on and it was determined that the sample adequately flowed in the equipment to be coated. Thirty-two milliliters of Stock Solution B (FOS, flavor agent, and water) was applied to the rotating Glycopulp™. After applying Stock Solution B, 17.5 grams of chicory pulp (1 mm screen size) was applied as a drying agent. Drying can also be achieved by low temperature air.

| Trial 2, Flavor Added | |
|---|---|
| Item | Amount |
| Stock Solution B: | |
| bioSecure ™ FOS | 11 grams |
| Milk Buds ™ | 1.2 mls |
| Water | 2 liters |
| Glycopulp | 320 grams |
| Chicory Pulp | 17.6 grams |

The source of fructo-oligosaccharide (FOS) in bioSecure™ FOS is derived from chicory roots. Chicory roots are a natural source of inulin; a carbohydrate made up of fructose polymers (fructan). The fructan cannot be metabolized by monogastrics, which lack the enzyme inulinase. Consequently, fructan passes on to the lower intestine where it is fermented by lactic acid producing bacteria such as *Bifidobacterium*. Gram negative bacteria such as *Escherichia coli* are unable to ferment or grow on fructan; thereby a natural selection will take place promoting beneficial bacteria in the lower intestine.

The following analysis of bioSecure™ FOS is exemplary only. As inulin and fructo-oligosaccharide are natural products, their exact composition will vary from crop to crop and from year to year. Additionally, the enzymatic breakdown of inulin with inulinase can vary. Neosugars are produced by an enzymatic reaction and can also vary in the end result.

| Analysis of bioSecure ™ FOS | |
|---|---|
| Item | % |
| Dry Matter | 95 |
| Carbohydrate Content | 99.9 |
| Ash | 0.1 |
| Carbohydrates | |
| Free Sugars | 8.2 |
| Glucose | 0.7 |
| Fructose | 2.9 |
| Sucrose | 4.6 |
| DP 1-10 | 41.1 |
| DP 11-20 | 30.0 |
| DP 21-30 | 17.5 |
| DP 31-40 | 7.7 |
| DP 41-50 | 2.6 |
| DP 51-60 | 1 |
| DP 3-20 | 61.8 |
| Average $DP_n$ | 6.6 |

Average $DP_n$ = The average degrees of polymerization of the product.

| Specifications of bioSecure ™ FOS | | |
|---|---|---|
| Analysis | Specification | Results |
| Dry Matter (%) | 95% Minimum | 97.1% |
| Ash (% of DM) | 0.5% Maximum | 0.1% |
| Carbohydrate content (% of DM) | 99.5% Minimum | 99.9% |
| Free Sugars (% of DM) | 10% Maximum | 9.1% |
| Fiber (% of DM) | 90% Minimum | 90.8% |
| Total Plate Count | 10,000 cfu/gm Maximum | 110 cfu/gm |
| Yeasts | 20 cfu/gm Maximum | <10 cfu/gm |
| Molds | 20 cfu/gm Maximum | <10 cfu/gm |
| Coliforms | 0 cfu/gm | 0 cfu/gm |

Having described the invention, alternatives and embodiments may occur to one of skill in the art. It is intended that such modifications and equivalents shall be included within the scope of the following claims.

I claim:

1. A composition comprising:
   a) a component selected from the group consisting of: essential oil, *Lactobacillus*, *Bifidobacterium*, and a combination thereof; and
   b) fructo-oligosaccharide (FOS) having a degree of polymerization (dp) in the range of 2 to 20 units and an average dp of 2 to 10,
   wherein said component is coated with said FOS to form a FOS-coated composition suitable for selective delivery to the colon of a monogastric animal.

2. The composition of claim 1, where the FOS has an average dp of 6.6.

3. The composition of claim 1, where the FOS is admixed with a flavoring agent.

4. A method for delivering a component to the colon of a monogastric animal, the method comprising administering to the animal the composition of claim 1.

5. A feed supplement comprising the composition of claim 1.

6. The composition of claim 1, wherein said FOS coating protects said composition from degradation in the stomach and small intestine of a monogastric animal.

7. The composition of claim 1, wherein said component is selectively delivered on degradation of the FOS coating in the colon of a monogastric animal.

8. A composition comprising:
a) a component selected from the group consisting of: essential oil, *Lactobacillus*, *Bifidobacterium*, spice, mineral, nutrient, nutraceutical, drug, a combination thereof; and
b) fructo-oligosaccharide (FOS) having a degree of polymerization (dp) in the range of 2 to 20 units and an average dp of 2 to 10,
wherein said component is coated with said FOS, said FOS-coating enabling selective release of said component in the colon of a monogastric animal.

9. The composition of claim 8, wherein said component is selectively released on degradation of the FOS coating in the colon of a monogastric animal.

10. The composition of claim 8, where the FOS has an average dp of 6.6.

11. The composition of claim 8, where the FOS is admixed with a flavoring agent.

12. The composition of claim 8, wherein said FOS coating protects said composition from degradation in the stomach and small intestine of a monogastric animal.

13. A feed supplement comprising the composition of claim 8.

14. A method of delivering a component to the colon of a monogastric animal comprising: orally administering the coated component of claim 8 to the animal.

15. The method of claim 14 wherein the component is *Lactobacillus* or *Bifidobaterium*.

16. The method of claim 14 wherein the component is a nutraceutical.

17. The method of claim 14 wherein the component is a drug.

18. The method of claim 14 wherein said component comprises a spice.

19. The method of claim 14 wherein said component comprises a nutraceutical.

20. A method for delivering a component to the colon of a monogastric animal, the method comprising administering to the animal the composition of claim 8.

* * * * *